United States Patent [19]

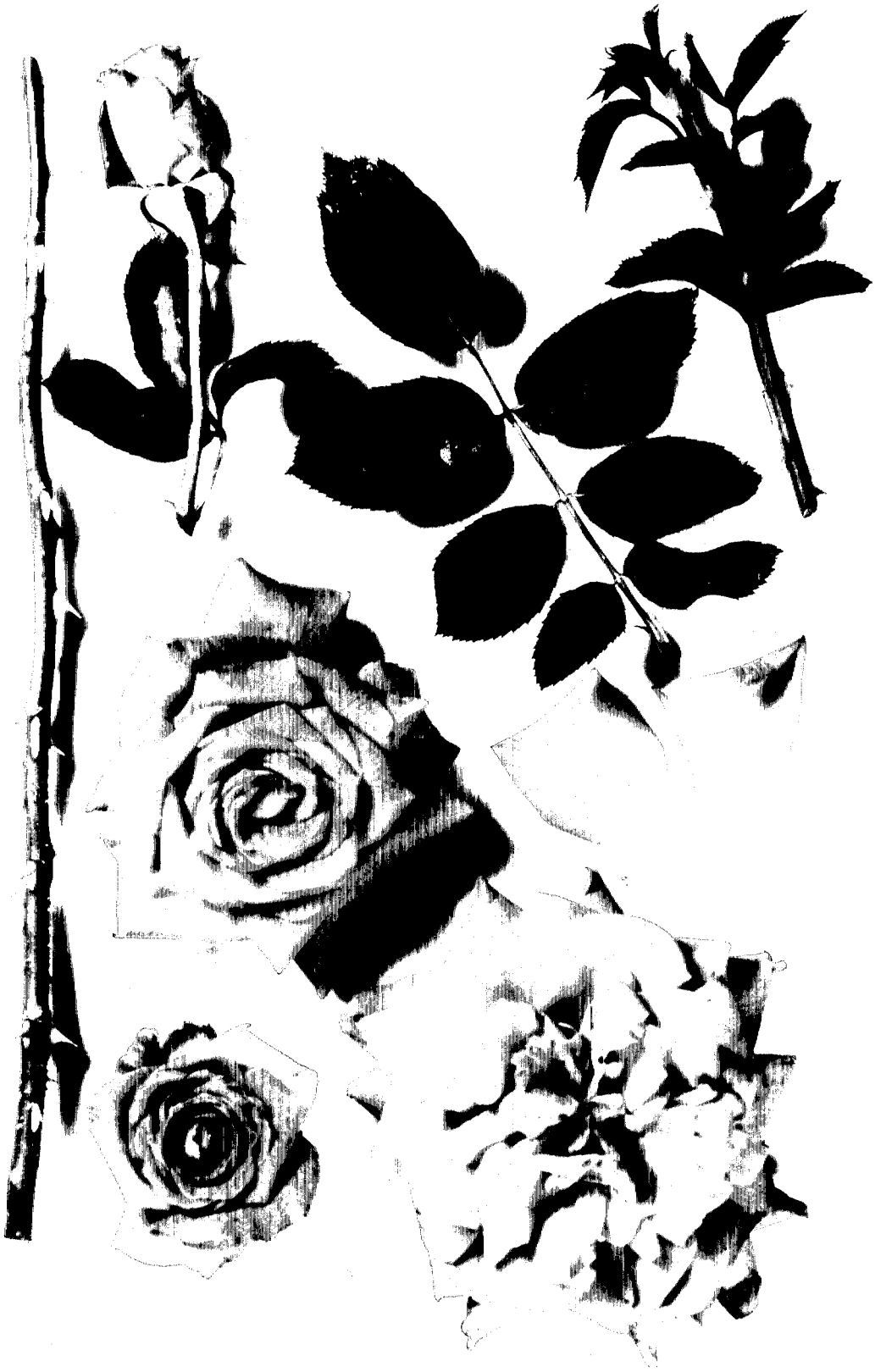

Warriner

[11] Patent Number: Plant 5,572

[45] Date of Patent: Oct. 15, 1985

[54] ROSE PLANT JACREP

[75] Inventor: William A. Warriner, Tustin, Calif.

[73] Assignee: Jackson & Perkins Company, Medford, Oreg.

[21] Appl. No.: 557,200

[22] Filed: Dec. 2, 1983

[51] Int. Cl.[4] ..... A01H 5/00

[52] U.S. Cl. ..... Plt./20

[58] Field of Search ..... Plt./20

*Primary Examiner*—James R. Feyrer

*Attorney, Agent, or Firm*—Klarquist, Sparkman, Campbell, Leigh & Whinston

[57] ABSTRACT

A hybrid tea rose variety having tall, upright growth habit, buds whose opening is not impaired by cool weather in the spring season, red colored petals with defined yellow area at point of attachment, light fragrance and good resistance to rose powdery mildew.

1 Drawing Figure

1

This present invention relates to a new and distinct variety of rose plant of the hybrid tea class which was originated by me by crossing an unnamed variety with the variety Proud Land, U.S. Plant Pat. No. 2,737.

The primary objective of this breeding was to produce a new rose variety combining the characteristics of vigor and color of both parents. This objective was substantially achieved along with other desirable improvements as evidenced by the following unique combination of characteristics which are outstanding in the new variety and which distinguish it from its parents, as well as from all other varieties of which I am aware:

1. Tall, upright habit of growth, with less spreading than Proud Land or Mr. Lincoln, U.S. Plant Pat. No. 2,370.
2. Opening of buds not impaired by cool weather in spring season as observed at Irvine, Calif.
3. Uniform red color near R.H.S. 46B except lighter shades on lower side of petals.
4. Pronounced, well defined area of yellow at point of attachment.
5. Light fragrance.
6. Good resistance to rose powdery mildew.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unnamed variety.

*Pollen parent.*—Proud Land, U.S. Plant Pat. No. 2,737.

Classification:

*Botanical.*—Rosa hybrid.

*Commercial.*—Hybrid tea.

2

FLOWER

Observations made from specimens grown at Irvine, Calif. in September.

Blooming habit: Continuous.

Bud:

*Size.*—1¼" When petals start to unfurl.

*Form.*—Long, blunt top.

*Color.*—When sepals first divide, slightly darker than Red 53B. When half blown; upper side of petals near Red 46B; lower side of petals mildly mottled, mostly near Red 46D and 46C.

*Sepals.*—Color: Outer surface Green 138A without glands or pubescence. Three appendaged sepals heavily appendaged. Two unappendaged sepals hairy edged.

*Receptacle.*—Color: Green 138A. Shape: Funnel. Size: Large, broad. Surface: Smooth.

*Peduncle.*—Length: Short. Surface: Glandular. Color: Light green. Strength: Stiff, erect, heavy.

*Opening.*—Spiral, slow.

Bloom:

*Size.*—Medium. Average open size: 4½".

*Borne.*—Singly.

*Stems.*—Long, strong.

*Form.*—When first open, high center. Permanence: Outer petal edges slightly curled.

*Petalage.*—Number of petals under normal conditions: 40.

*Color.*—Center of flower: Upper side of petals Red 46B; reverse side of petals much lighter than upper side, mostly Red 46D; base of petals have large area at point of attachment, Yellow 13B. General tonality from a distance Red 46B.

*Variegations.*—Occasional white streaks in outer petals.

*Discoloration.*—General tonality at end of first day: Red 46B. Third day: Red 46B.

*Fragrance.*—Slight.

Petals:

*Texture.*—Thin.

*Shape.*—Oval.

*Form.*—Edges slightly quilled.

*Arrangement.*—Informal, not perfectly imbricated. Petaloids in center: many, large.

*Persistence.*—Drop off cleanly.

*Lastingness.*—On the plant, long. As cut flower, long.

Reproductive parts:

*Anthers.*—Medium. Color: Yellow. Arrangement: Regular around styles, mixed with petaloids.

*Filaments.*—Color: Yellow.

*Pollen.*—Gold yellow.

*Styles.*—Color: Purplish-red.

*Stigmas.*—Color: Yellow.

PLANT

Form: Bush.

Growth: Very vigorous, upright, reaching 6′ to 6½′ at Irvine, Calif.

Foliage: Number of leaflets on normal mid-stem leaves: 5 to 7.

*Size.*—Large to medium.

*Quantity.*—Normal.

*Color.*—New foliage: Grayed Purple 187A. Old foliage: Green 137A.

Leaflets:

*Shape.*—Oval pointed.

*Texture.*—Leathery on upper side.

*Edge.*—Serrated.

*Serration.*—Single, small.

*Petiole.*—Rachis: Color: Green. Underside: Prickles. Upperside: Glandular.

*Stipules.*—Long, bearded.

*Disease resistance.*—Resistant to mildew, blackspot under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base: many. On laterals from stalk: many.

*Form.*—Long, hooked downward.

*Color when young.*—Pale brown.

*Position.*—Irregular.

Small prickles:

*Quantity.*—On main stalks, many. On laterals, many.

I claim:

1. A new and distinct variety of rose plant of the hybrid tea class, substantially as herein shown and described, characterized particularly as to novelty by the unique combination of its tall, upright plant, uniform red, lightly fragrant blooms, and mildew resistant foliage.

* * * * *